US00PP27558P2

(12) United States Plant Patent
Verschoor

(10) Patent No.: US PP27,558 P2
(45) Date of Patent: Jan. 17, 2017

(54) ***PHLOX* PLANT NAMED 'VERSCAN'**

(50) Latin Name: *Phlox paniculata*
Varietal Denomination: Verscan

(71) Applicant: Janus Verschoor, Haarlem (NL)

(72) Inventor: Janus Verschoor, Haarlem (NL)

(73) Assignee: A. VERSCHOOR HORTICULTURE IMPORT-EXPORT B.V., Haarlem (NL)

( * ) Notice: Subject to any disclaimer, the term of this patent is extended or adjusted under 35 U.S.C. 154(b) by 0 days.

(21) Appl. No.: 14/756,960

(22) Filed: Nov. 2, 2015

(51) Int. Cl.
*A01H 5/02* (2006.01)

(52) U.S. Cl.
USPC ..... Plt./320

(58) Field of Classification Search
USPC ..... Plt./320
See application file for complete search history.

*Primary Examiner* — Annette Para
(74) *Attorney, Agent, or Firm* — Penny J. Aguirre

(57) ABSTRACT

A new cultivar of *Phlox*, 'Verscan', characterized by its very dwarf and compact plant habit, its bi-colored flowers that are bright red-purple and white in color, its leaves with a thick substance, its healthy plant growth, its strong basal branching, and its low susceptibility to powdery mildew.

2 Drawing Sheets

Botanical classification: *Phlox paniculata.*
Cultivar designation: 'Verscan'.

BACKGROUND OF THE INVENTION

The present invention relates to a new and distinct cultivar of *Phlox* plant, botanically known as *Phlox paniculata* 'Verscan' and will be referred to hereafter by its cultivar name, 'Verscan'. The new cultivar represents a new herbaceous perennial grown for landscape use.

The Inventor discovered 'Verscan' as a chance seedling in August of 2011 in a field planted with various *Phlox* cultivars and unnamed proprietary *Phlox* plants in Haarlem, The Netherlands. The parentage of 'Verscan' is therefore unknown.

Asexual propagation of the new cultivar was first accomplished by stem cuttings in Haarlem, The Netherlands in September of 2011 by the Inventor. Asexual propagation by stem cuttings and division has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Verscan' as a unique cultivar of *Phlox*.

1. 'Verscan' exhibits a dwarf and compact plant habit.
2. 'Verscan' exhibits bi-colored flowers that are bright red-purple and white in color.
3. 'Verscan' exhibits leaves with a thick substance.
4. 'Verscan' exhibits strong basal branching.
5. 'Verscan' exhibits some resistance to powdery mildew.
6. 'Verscan' exhibits healthy plant growth.

'Verscan' can be compared to the cultivars 'Peppermint Twist' (U.S. Plant Pat. No. 18,196) and 'Candy Floss' (U.S. Plant Pat. No. 18,163). 'Peppermint Twist' is similar to 'Verscan' in having flowers that are bi-color and in having some resistance to powdery mildew. 'Peppermint Twist' differs from 'Verscan' in having stems that are longer in length, in having flowers that are pinker in color, and in having less basal branching. 'Candy Ross' is similar to 'Verscan' in branching habit and in having resistance to powdery mildew. 'Candy Ross' differs from 'Verscan' in having flowers that are not bi-colored and coral pink in color and in having stems that are longer in length.

BRIEF DESCRIPTION OF THE DRAWINGS

The accompanying colored photographs illustrate the overall appearance and distinct characteristics of the new *Phlox*. The photographs were taken of an 18 month-old plant (from an un-rooted cutting) of 'Verscan' as field grown in Haarlem, The Netherlands and placed in a container for the photographs.

The photograph in FIG. 1 is a view of a plant of 'Verscan' in bloom.

Figure 1:
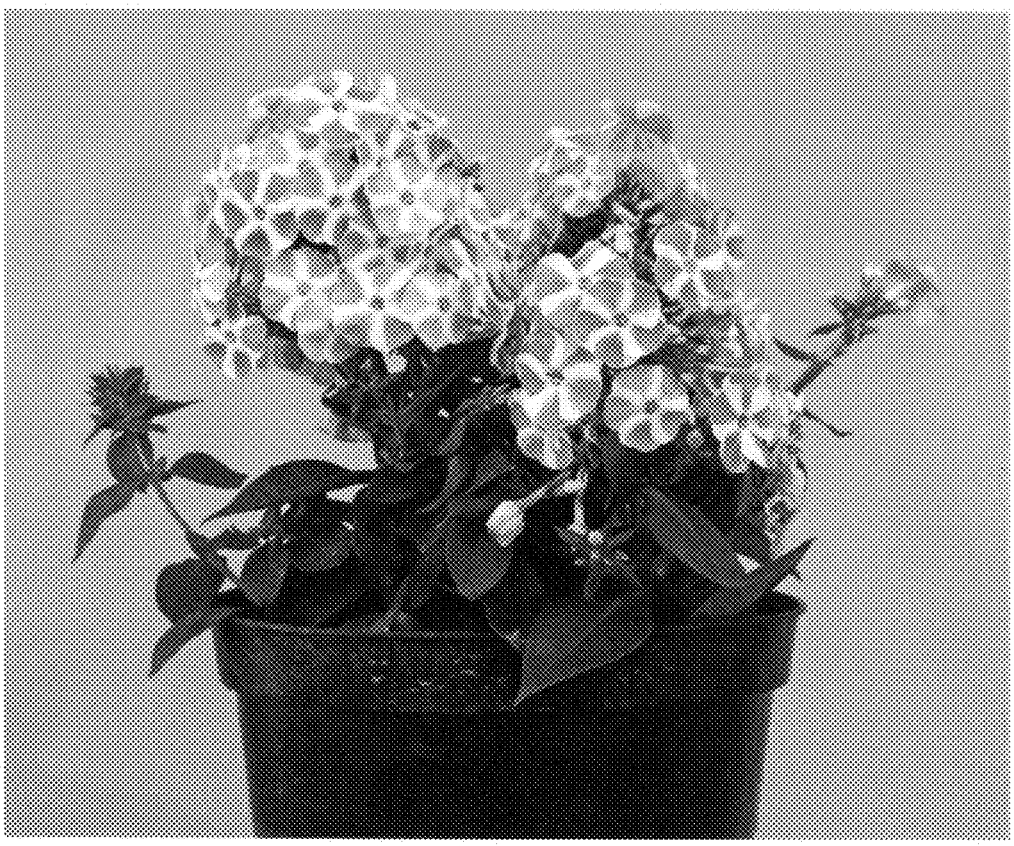
Figure 2:
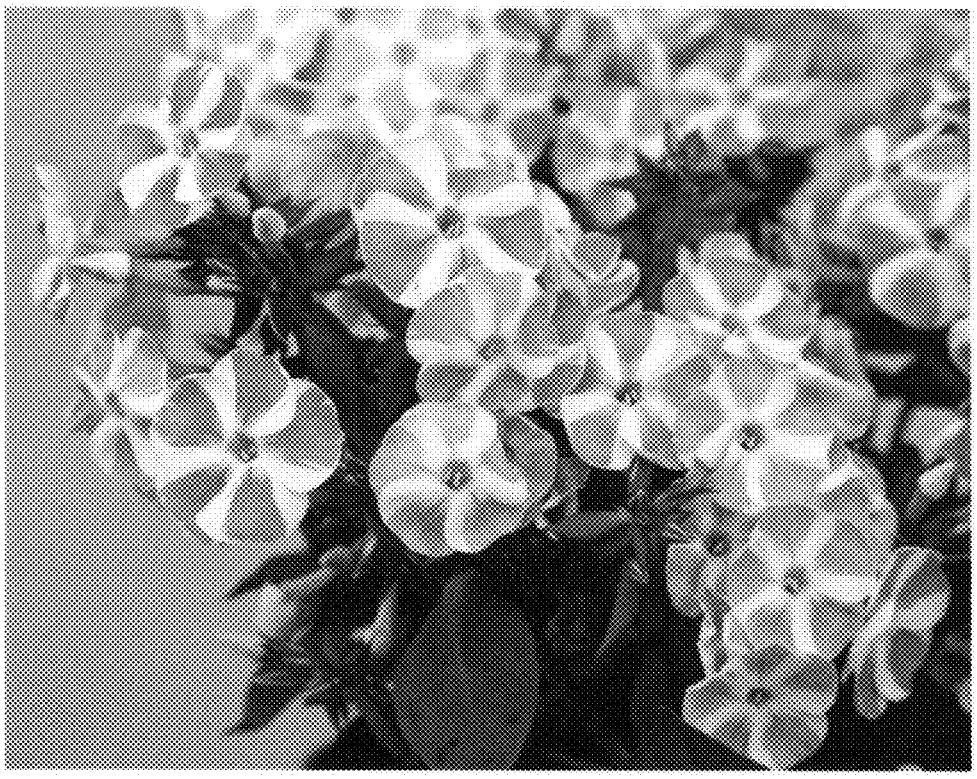

The photograph in FIG. 2 is a close-up view of an inflorescence of 'Verscan'.

Figure 3:
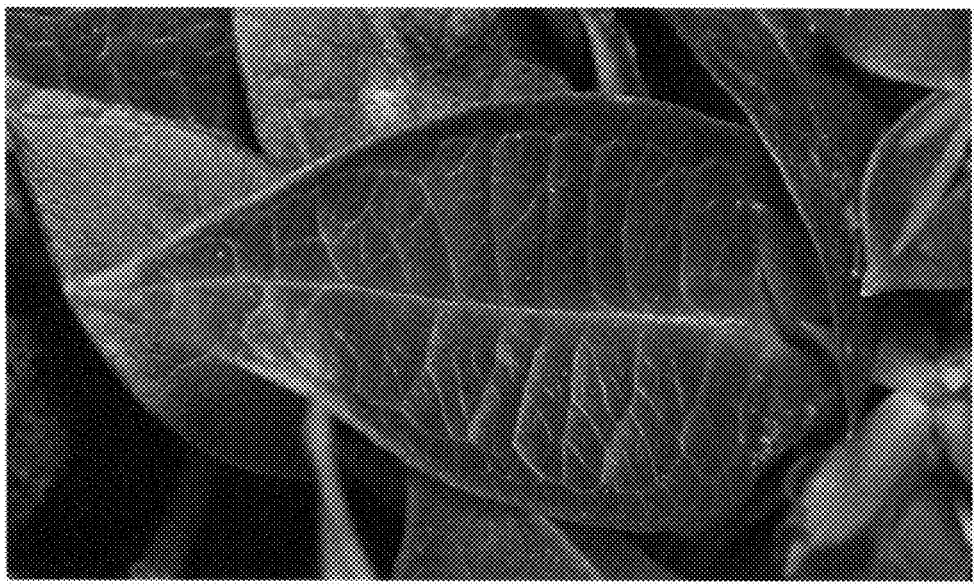

The Photograph in FIG. 3 provides a close-up view of a leaf of 'Verscan'.

The colors in the photographs may differ slightly from the color values cited in the detailed botanical description, which accurately describe the colors of the new *Phlox*.

DETAILED BOTANICAL DESCRIPTION OF THE PLANT

The following is a detailed description of 18 month-old plants (from an un-rooted cutting) of the new cultivar as field grown in Haarlem, The Netherlands. The plants were grown under average day temperatures of 14° C. to 30° C. and average night temperatures of 8° C. to 18° C. The phenotype of the new cultivar may vary with variations in environmental, climatic, and cultural conditions, as it has not been tested under all possible environmental conditions. The color determination is in accordance with The 2015 R.H.S. Colour Chart of The Royal Horticultural Society, London, England, except where general color terms of ordinary dictionary significance are used.

General description:

*Blooming period*.—Early July to September in the Netherlands.

*Plant type*.—Herbaceous perennial.

*Plant habit*.—Very dwarf and compact.

*Height and spread*.—Reaches an average of 30 cm in height and about 40 cm in spread in the landscape.

*Hardiness*.—At least in U.S.D.A. Zones 4 to 9.

*Diseases*.—Has shown some resistance (less susceptibility when grown under the same circumstances as other cultivars) to powdery mildew caused by *Erysiphe cichoracea*.

*Root description*.—Fibrous.

*Growth rate*.—Moderate.

*Propagation*.—Stem cuttings, division also possible.

*Root initiation*.—About 30 days in summer.

*Root development*.—About 28 weeks from a rooted cutting to fully develop in a 1.5 liter container.

Stem description:

*Branching habit*.—Flowering stems and lateral branches grow from base.

*Stem quantity*.—Average of 10 flowering stems.

*Stem size*.—12.3 cm in length (excluding inflorescence), average of 3 mm in diameter.

*Stem shape*.—Round.

*Stem strength*.—Strong.

*Stem color*.—144B.

*Stem surface*.—Glabrous and moderately glossy.

*Stem aspect*.—Held in an average angle of 45° to soil level (=0°), varying between 40° and 60°.

*Internode length*.—An average of 2.2 cm.

*Branching habit*.—Basal flowering stems, well-branched.

Foliage description:

*Leaf shape*.—Elliptic and slightly carinate.

*Leaf division*.—Simple.

*Leaf base*.—Truncate.

*Leaf apex*.—Apiculate.

*Leaf venation*.—Pinnate, upper side 144A to 144B, lower side 144C.

*Leaf margins*.—Slightly revolute, entire, very finely serrate, not visible, but can feel they are there.

*Leaf attachment*.—Petiolate.

*Leaf arrangement*.—Opposite.

*Leaf surface*.—Very slightly rugose, upper side very slightly glossy, lower side matte.

*Leaf color*.—Young upper surface; 143A, young lower surface; 143B, mature upper surface; NN137A, mature lower surface; 147B.

*Leaf size*.—An average of 7.4 cm in length and 3.2 cm in width.

*Leaf quantity*.—An average of 12 (6 pairs).

*Petioles*.—V-shaped, an average of 2.5 mm in height, 4 mm in width and 2.5 mm in length, N144D in color, both surfaces are glabrous.

Flower description:

*Inflorescence type*.—Compound terminal panicle.

*Lastingness of inflorescence*.—About 3 to 4 weeks from the opening of the first flower to senescence of last flower, individual flower lasts about 10 days.

*Inflorescence size*.—An average of 10 cm in height and width.

*Flower fragrance*.—Moderate, sweet and pleasant *phlox* fragrance.

*Flower number*.—Average of 90 per inflorescence.

*Flower aspect*.—Upright to outward.

*Flower bud*.—An average of 2.2 cm in length and up to 5 mm in width, narrow obovate in shape, color; NN155C, top 76C, immature tube 145B, immature calyx 146B, tinged 200A, glabrous surface.

*Flower form*.—Explanate with tubular base.

*Flower size*.—An average of 2.8 cm in diameter and 2.4 cm in depth.

*Petals*.—5, self-cleaning, upper surface velvety, lower surface slightly glossy, outer surface of tube densely covered with very short soft hairs; average of 0.5 mm in length and NN155D in color, rotate and moderately overlapping arrangement, petals are fused 65% into tube, spathulate in shape, margins entire, obtuse to broad and slightly retuse, average of 3.6 cm in length (lower 2.3 cm fused into tube), average of 1.7 cm in width, color when opening upper side; 75B, broadly margined NN155D, tube 145D, color when opening lower side; 75B, broadly margined NN155D, tube 156D, color fully open upper side; 73A, broadly margined NN155D, tube N77D, color fully open lower side; 75B, broadly margined NN155D, tube 157C to 157D, petal color fading to 67B, broadly margined NN155D, tube N77B.

*Calyx*.—Campanulate in form, an average of 9 mm in length and 3 mm in width.

*Sepals*.—5, base lower 15% fused, linear in shape, margins entire, apex narrowly apiculate, an average of 9 mm in length and 1 mm in width, surface is glabrous and matte, color; immature upper surface 143A to 143B slightly tinged 200A, immature lower surface 146B tinged 200A, mature upper surface 144B, mature lower surface color between 144A and 146C slightly tinged with 200B.

*Peduncles*.—Oval in shape, strong, primary an average of 6.8 cm in length and 2 cm in width, secondary an average of 2.6 cm in length and 1.5 mm in width, primary held upright, secondary held at about a 45° angle, glabrous surface, color 145A.

*Pedicels*.—Oval in shape, strong, an average of 5 mm in length and 1 mm in width, glabrous surface, held at. an average angle of 45° (0°=straight on top of peduncle), color 144B.

Reproductive organs:

*Gynoecium*.—Pistil; 1, 1.8 cm in length, stigma; cleft (3-parted), 150C in color, style; 1.65 cm in length, 150C to 150D in color, ovary; superior and 143A in color.

*Androcoecium*.—5 stamens, anthers; basifixed and oblong in shape, 2 mm in length and 160D in color, filaments; implanted in petal, 5 mm in length, N155B in color, pollen is low in quantity and 155A in color.

*Seeds*.—None observed.

It is claimed:

1. A new and distinct cultivar of *Phlox* plant named 'Verscan' as herein illustrated and described.

* * * * *